US00PP34192P2

(12) United States Plant Patent
Valin

(10) Patent No.: US PP34,192 P2
(45) Date of Patent: May 3, 2022

(54) ***WEIGELA* PLANT NAMED 'MAGIC CARPET'**

(50) Latin Name: *Weigela florida*
Varietal Denomination: Magic Carpet

(71) Applicant: Branded Garden Products Ltd., Southampton (GB)

(72) Inventor: Charles Valin, Ipswich (GB)

(73) Assignee: Branded Garden Products, Ltd., Southampton (GB)

( * ) Notice: Subject to any disclaimer, the term of this patent is extended or adjusted under 35 U.S.C. 154(b) by 0 days.

(21) Appl. No.: 17/496,510

(22) Filed: Oct. 7, 2021

(51) Int. Cl.
*A01H 6/00* (2018.01)
*A01H 5/02* (2018.01)

(52) U.S. Cl.
USPC ..... Plt./226

(58) Field of Classification Search
USPC ..... Plt./226
CPC ..... A01H 6/00; A01H 5/02
See application file for complete search history.

*Primary Examiner* — Keith O. Robinson
(74) *Attorney, Agent, or Firm* — Weatherly IP Solutions, LLC; Barbara Campbell

(57) ABSTRACT

A new cultivar of *Weigela* plant named 'Magic Carpet' that is characterized by upright narrow vase-shaped plant habit, and foliage which ranges between golden yellow and bright orange-red in color in the spring, with older foliage becoming light green during the summer months, and bearing profuse red-purple flowers in spring, is disclosed.

2 Drawing Sheets

Figure 1:
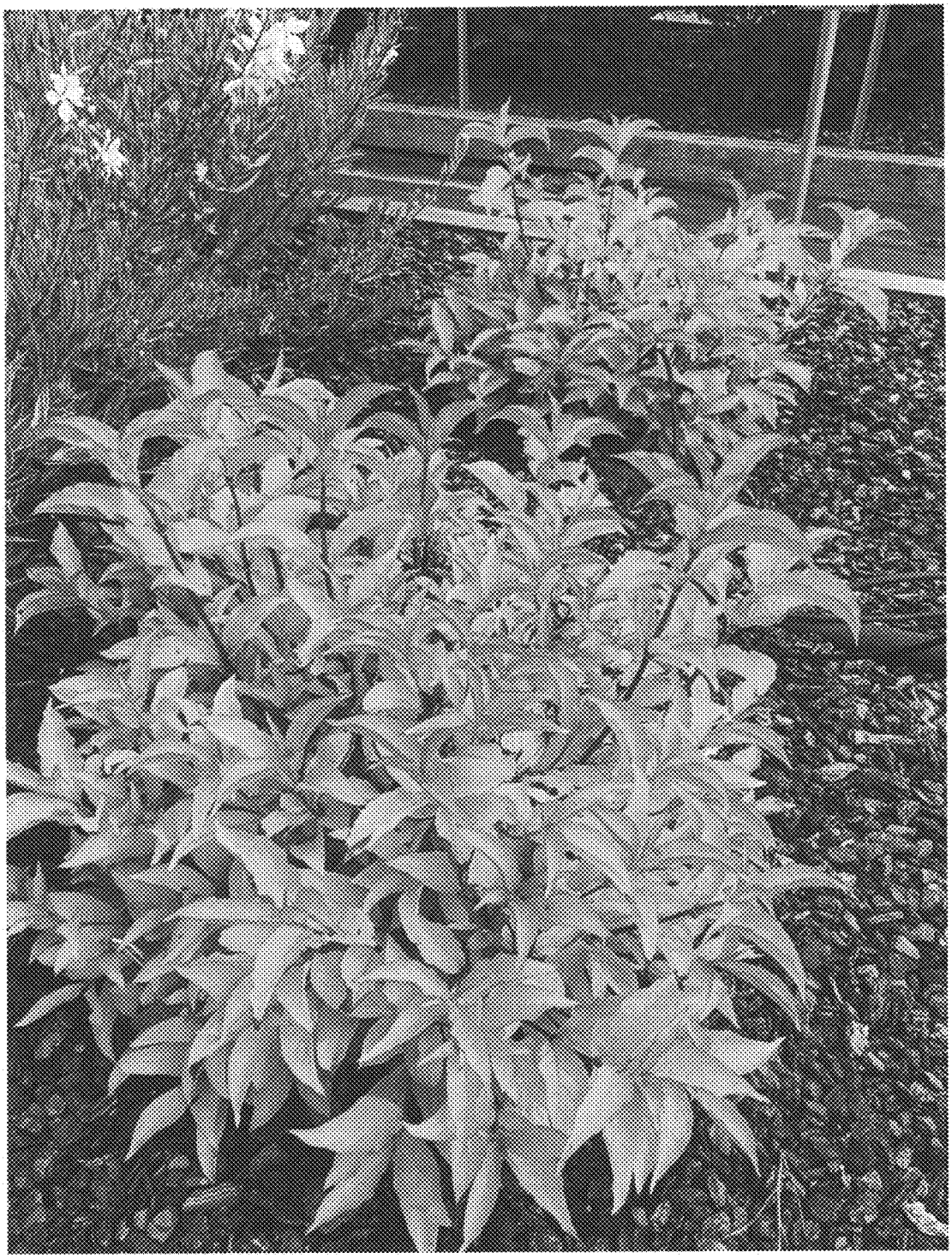

Genus and species: *Weigela florida.*
Variety denomination: 'Magic Carpet'.

BACKGROUND OF THE NEW PLANT

The present invention relates to a new and distinct cultivar of *Weigela*, grown as an ornamental plant for use in the garden and landscape. The new cultivar is known botanically as *Weigela florida* and will be referred to hereinafter by the cultivar name 'Magic Carpet'.

'Magic Carpet' was developed and selected by the inventor for its bright golden yellow foliage which also exhibits orange-red coloration especially in spring prior to flowering. 'Magic Carpet' is a colorful accent plant from spring through fall.

The inventor selected 'Magic Carpet' in 2018. 'Magic Carpet' was raised by the inventor at a greenhouse and field nursery in Ipswich, Suffolk, United Kingdom. The inventor raised 'Magic Carpet' from seed collected from the open-pollination of proprietary seedling code 'WG16016' as the female parent (unpatented). The male parent is an unidentified proprietary unpatented seedling raised by the inventor and retained in the inventor's collection of breeding material.

The inventor first asexually reproduced 'Magic Carpet' in 2018 by the method of softwood cuttings. Since that time, the unique characteristics of the new *Weigela* plant have been uniform, stable and reproduced true to type in successive generations of asexual reproduction.

SUMMARY

The following traits have been repeatedly observed and represent the characteristics of the new *Weigela* cultivar 'Magic Carpet'. 'Magic Carpet' has not been tested under all possible conditions and phenotypic differences may be observed with variations in environmental, climatic and cultural conditions, however, without any variance in genotype.

1. 'Magic Carpet' exhibits a compact mounding growth habit.
2. By the second year of growth in a 3-gallon container, plants of 'Magic Carpet' achieve a height of 60 cm to 75 cm and a width (at full height) of 45 cm to 60 cm.
3. A mature plant of 'Magic Carpet' which is growing in-ground achieves a height of 1 meter and a width at full height of 75 cm to 80 cm.
4. The emerging spring foliage color, prior to first flowering, of 'Magic Carpet' ranges between golden yellow and bright orange-red. The orange-red coloration is especially pronounced on the new spring growth.
5. In the summer months, the orange-red coloration becomes subdued and the older and lower foliage becomes light green in color.
6. The flowers and flower buds of 'Magic Carpet' are red-purple in color.
7. The flowers of 'Magic Carpet' are borne typically in clusters of eight to twelve per inflorescence.
8. 'Magic Carpet' flowers profusely in mid-spring and then sporadically during summer.
9. 'Magic Carpet' grows well in moist well-drained soils in full sun to partial shade.
10. 'Magic Carpet' is hardy at least to USDA Zone 5.

BRIEF DESCRIPTION OF THE PHOTOGRAPHS

The accompanying color photographs illustrate the overall appearance of the new *Weigela* variety 'Magic Carpet' showing colors as true as it is reasonably possible to obtain in colored reproductions of this type. Colors in the photographs may differ from the color values cited in the detailed botanical description, which accurately describe the actual colors of the new variety 'Magic Carpet'.

FIG. 1 depicts, in the foreground, a whole plant of 'Magic Carpet' in early spring before flowering. The illustrated plant is eighteen-months-old and has been grown entirely outdoors in Oxnard, Calif.

Figure 2:
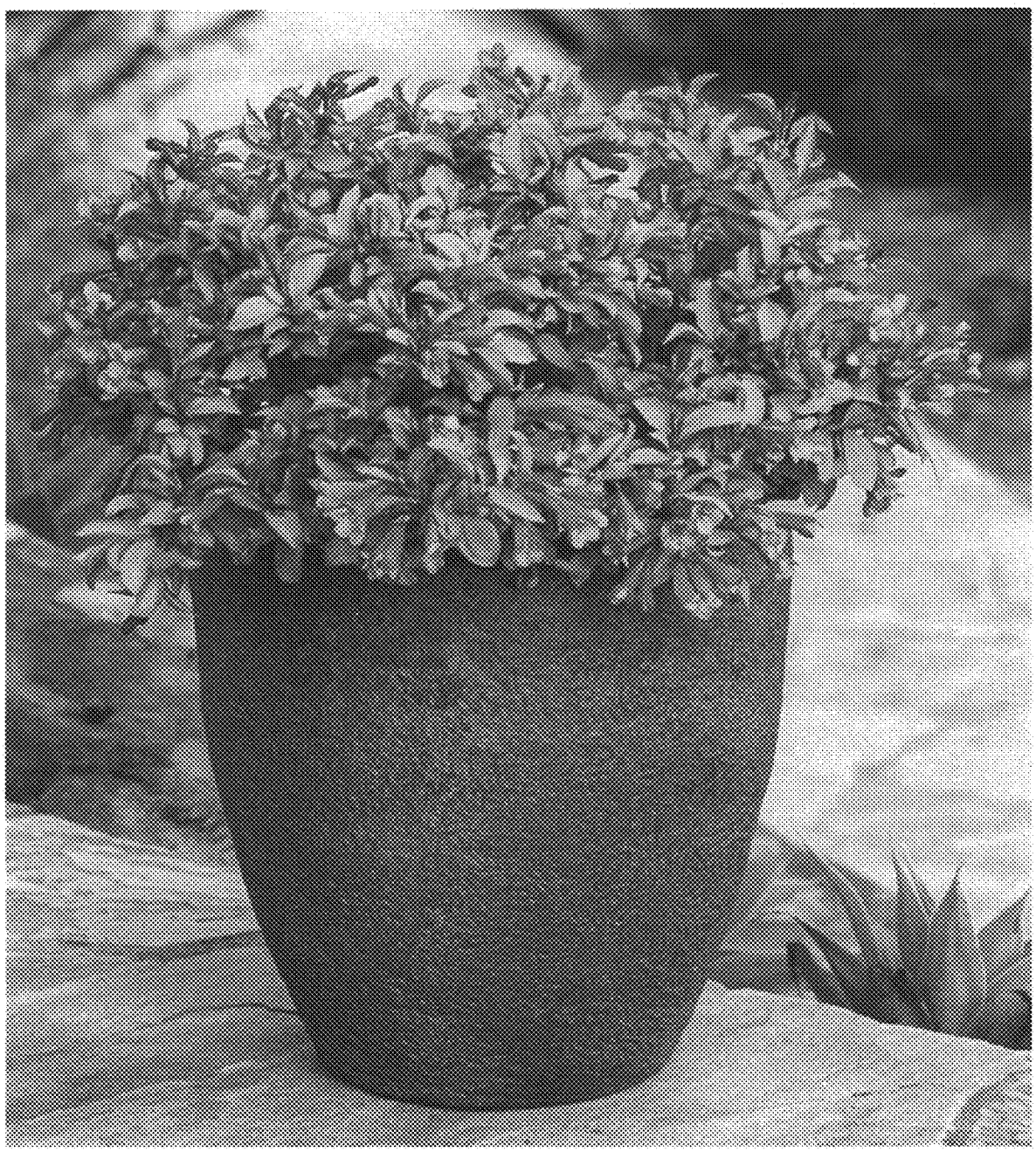

FIG. 2 depicts a whole plant of 'Magic Carpet' in early summer when the plant is in full bud and flower and the golden yellow spring foliage is turning to pale green summer foliage. The illustrated plant is two years old and has been grown outdoors in Oxnard, Calif. and has been transplanted into a 5-gallon container Photographs were taken in Oxnard, Calif. No chemicals were used to treat the plant. All photographs were made using conventional techniques and although colors may appear different from actual colors due to light reflectance they are as accurate as possible by conventional photography.

BOTANICAL DESCRIPTION OF THE PLANT

The following is a detailed description of the new cultivar 'Magic Carpet'. Data was collected from two-year old plants grown in 3-gallon containers in Oxnard, Calif. The color determinations are in accordance with the 2007 edition of The Colour Chart of The Royal Horticultural Society, London, England, except where general color terms of ordinary dictionary significance are used. No chemicals were used to treat the plants. Growing conditions are typical of other *Weigela*.

Botanical classification: *Weigela*.
- *Variety*.—'Magic Carpet'.
- *Species*.—*Florida*.

Parentage:
- *Female parent*.—Proprietary seedling code 'WG16016' (unreleased, unpatented).
- *Male parent*.—Unidentified proprietary seedling.

Plant description:
- *Growth habit*.—Compact, mounding.
- *Use*.—In containers and in the landscape.
- *Suitable container sizes*.—1 to 3-gallon containers.
- *Dimensions in second year in a 3-gallon container*.—60 cm to 75 cm in height, and 45 cm to 60 cm in width measured at full plant height.
- *Dimensions when mature in open ground*.—1 meter in height, 75 cm to 80 cm. in width measured at full plant height.
- *Hardiness*.—At least hardy to USDA Zone 5.
- *Propagation*.—Stem cuttings.
- *Time to initiate roots*.—5 to 6 weeks are required to produce roots on an initial cutting.
- *Crop time*.—One year to 18 months are required to produce a finished one-gallon container from a rooted cutting.
- *Root system*.—Fibrous.
- *Light*.—Plant in full sun or partial shade.
- *Soil*.—Plant in moist but well drained soil.
- *Type*.—Deciduous shrub.
- *Seasonal interest*.—Bright and colorful foliage in spring.

Stem:
- *Shape*.—Terete.
- *Dimensions*.—12 cm to 15 cm in length, 8 mm diameter at soil level.
- *Color*.—198D.
- *Surface*.—Lignified in second year, rough, glabrous, lenticels present.
- *Lenticels*.—Spaced approximately 5 mm apart, roughly circular, diameter 2 mm, raised 1 mm, colors range between 156D and 198A.

Branches:
- *Branch stem dimensions*.—50 cm to 65 cm in length, 5 mm to 8 mm in diameter.
- *Shape*.—Terete.
- *Internode length*.—4 cm to 6 cm.
- *Color* (*current year's growth*).—182A.
- *Color* (*previous year's growth, lignified*).—198D.
- *Surface*.—Smooth, pubescent, hairs fine, 1.0 mm to 1.5 mm in length, color NN155D.

Foliage:
- *Leaf arrangement*.—Opposite.
- *Leaf division*.—Simple.
- *Leaf shape*.—Ovate, longitudinally inwardly curved.
- *Leaf attachment*.—Petiolate.
- *Petiole dimensions*.—4 mm in length and 2 mm in width.
- *Petiole color*.—160A.
- *Leaf dimensions*.—80 mm in length, 32 mm in width.
- *Leaf surface* (*adaxial*).—Glabrous.
- *Leaf surface* (*abaxial*).—Glabrous, except vein midrib pubescent, hairs fine, less than 0.5 mm in length, color white.
- *Leaf color* (*spring growth, adaxial surface*).—2B, 7B, 151C are all individually present.
- *Leaf color* (*spring growth, abaxial surface*).—7B, 151C, 28C are all individually present, and 33A on the abaxial surfaces of the newly emerging growth.
- *Leaf color* (*summer foliage, adaxial surface*).—Ranges between pale yellow-green 154A and mid-green 144C.
- *Leaf color* (*summer foliage, abaxial surface*).—Ranges between pale yellow-green 154A and mid-green 144C. The color of the youngest tip growth (abaxial surface) ranges between 32B and 33A.
- *Leaf apex*.—Acute, occasionally acuminate.
- *Leaf base*.—Cuneate.
- *Leaf margin*.—Finely serrate, glabrous except leaf margin pubescent towards base, hair color white, hair length 1 mm to 2 mm.
- *Leaf venation pattern*.—Pinnate.
- *Veins* (*adaxial surface*).—Prominent midrib, slightly depressed, color 155A.
- *Veins* (*abaxial surface*).—Prominent midrib, raised approximately 1 mm, color 155A, surface puberulent.

Inflorescence:
- *Inflorescence form*.—Cymose. Present at each leaf axil until June when no more flowers are initiated as foliage growth continues.
- *Quantity of flowers per inflorescence*.—Typically, either 8 or 12 flowers per inflorescence, and occasionally 6 flowers or 14 flowers.

Flowers:
- *Flower aspect*.—Outward and upward facing.
- *Diameter of fully developed flower* (*at flower tube apex*).—18 mm to 20 mm.
- *Length of flower*.—35 mm to 38 mm.
- *Bud*.—Shape: Cylindrical, apex capitate. Color: Ranges between 53A and 53C. Dimensions: 25 mm in length, 10 mm in diameter immediately prior to opening. Surface: Tomentose.

*Bracteoles*.—Arrangement: Borne in pairs the base of peduncle. Shape: Narrowly lanceolate Dimensions: Longer bracteole 18 mm to 20 mm in length, 1 mm in width at base. Color: 152C. Surface: Glabrous.

*Peduncle*.—Dimensions: 15 mm to 18 mm in length and 1.5 mm to 2.5 mm in diameter. Shape: Round. Color: 183B. Surface: Puberulent, hairs fine, white.

*Calyx, sepals*.—Shape: Funnel-shaped. Calyx diameter: 3.5 mm measured across sepal apices. Sepals: 5 in number, longitudinally fused for 50%-80% of sepal length. Sepal dimensions: 8 mm to 10 mm in length, 2 mm in width. Sepal color (both surfaces): Ranges between 179A and 179B. Sepal surface (both surfaces): Matte, very lightly pubescent.

*Corolla*.—Shape: Salverform. Dimensions: 25 mm in length, 2 mm in diameter at base, 12 mm in diameter at base of petal lobes. Surface: Glabrous. Tube color: Adaxial surface: 60C. Abaxial surface: 65C with darker longitudinal striations 60C.

*Petals*.—Number: 5, fused. Shape: Equal, orbicular. Color (adaxial surface): 60C. Color (abaxial surface): 65C. Surface texture: Glabrous.

Reproductive organs:

*Number of stamens*.—5, fused at base.

*Dimensions*.—15 mm to 17mm in length, 0.5 mm to 0.75 mm in diameter.

*Filament color*.—65C towards base, becoming N155B towards anthers.

*Anther shape*.—Bifid, narrow elliptical.

*Anther dimensions*.—5 mm in length and 1 mm in width.

*Anther color*.—159C.

*Pollen color*.—159B.

*Pollen amount*.—Light to moderate.

*Number of pistils*.—1.

*Style*.—Terete, 26 mm in length and 1 mm in width.

*Style color*.—65A to 65C.

*Style surface*.—Glabrous.

*Stigma shape*.—Capitate, three-lobed.

*Stigma dimensions*.—4 mm in width and 2 mm in depth.

*Stigma color*.—199C.

*Ovary*.—Superior, ovoid, 1.5 mm in length and 1 mm in diameter, color 152A, smooth.

Fruit: None observed.

Seed: None observed.

Susceptibility or resistance to pests and diseases: None.

COMPARISON WITH PARENT

In comparison with 'Magic Carpet', the female parent grows with a similarly compact habit but bears chartreuse colored foliage throughout the season whereas the foliage color of 'Magic Carpet' ranges between golden yellow and bright orange-red in the spring, with older foliage becoming light green during the summer months. No comparison with the unidentified male parent is available.

COMPARISON WITH CLOSEST KNOWN VARIETY

'Magic Carpet' may be compared with *Weigela* plant named 'Wings of Fire' (U.S. Plant Pat. No. 21,920). Whereas both varieties, 'Magic Carpet' and 'Wings of Fire' are similarly compact in habit, the plant form of 'Magic Carpet' is mounding and the plant habit of 'Wings of Fire' is upright. The two varieties differ by foliage color and flower color. The foliage color of 'Magic Carpet' ranges between golden yellow and bright orange-red in the spring, with older foliage becoming light green during the summer months. The spring foliage color of 'Wings of Fire' is green with tinges of grey-orange, becoming mostly grey-orange in the summer months. The flowers of 'Magic Carpet' are slightly smaller than the flowers of 'Wings of Fire'. The flowers of 'Magic Carpet' are dark red-purple in color whereas the flowers of 'Wings of Fire' are paler pink-red in color.

I claim:

1. A new and distinct cultivar of *Weigela* plant named 'Magic Carpet' as described and illustrated herein.

* * * * *